United States Patent [19]

Burton

[11] Patent Number: 4,665,912
[45] Date of Patent: May 19, 1987

[54] SKIN MARKING DEVICE

[75] Inventor: Thomas A. Burton, Rochester, Minn.

[73] Assignee: Waters Instruments, Inc., Rochester, Minn.

[21] Appl. No.: 764,188

[22] Filed: Aug. 9, 1985

[51] Int. Cl.⁴ ............................................. A61B 17/00
[52] U.S. Cl. ................................ 128/303 R; 128/316; 128/329 R; 81/9.22
[58] Field of Search ................ 81/9.22; 401/221, 235, 401/232; 128/303 R, 316, 355, 329; 30/366; 33/18.2

[56] References Cited

U.S. PATENT DOCUMENTS

| | | | |
|---|---|---|---|
| 216,086 | 6/1879 | Gunning et al. | 30/366 |
| 473,207 | 4/1892 | Carey | 81/9.22 |
| 516,212 | 3/1894 | Lewis | 81/9.22 |
| 824,867 | 7/1906 | Houghton | 30/366 |
| 1,724,812 | 8/1929 | Waters | 81/9.22 |
| 3,382,577 | 5/1968 | Rieder | 30/366 |
| 4,031,783 | 6/1977 | Paul et al. | 81/9.22 |
| 4,508,106 | 4/1985 | Anges | 81/9.22 |

FOREIGN PATENT DOCUMENTS

| | | | |
|---|---|---|---|
| 252969 | of 1912 | Fed. Rep. of Germany | 401/232 |
| 2109056 | 5/1972 | France | 128/329 |
| 36060 | 2/1906 | Switzerland | 81/9.22 |
| 109137 | 3/1925 | Switzerland | 81/9.22 |
| 13539 | of 1900 | United Kingdom | 81/9.22 |
| 153084 | 10/1920 | United Kingdom | 81/9.22 |

Primary Examiner—Robert Peshock
Assistant Examiner—Cary E. Stone
Attorney, Agent, or Firm—James R. Haller

[57] ABSTRACT

A skin marking device comprising a finger-held tubular barrel having a narrow opening at one end, and a needle carried in the barrel and having a pointed end extending outwardly through the narrow barrel opening, the needle and opening forming an annular flow passage. A dye is carried within the barrel in flow communication with the annular flow passage to provide dye to the end of the barrel from when it may be drawn by contact with the skin to be marked. In one embodiment, the needle may be axially moved between extended and retracted positions.

9 Claims, 4 Drawing Figures

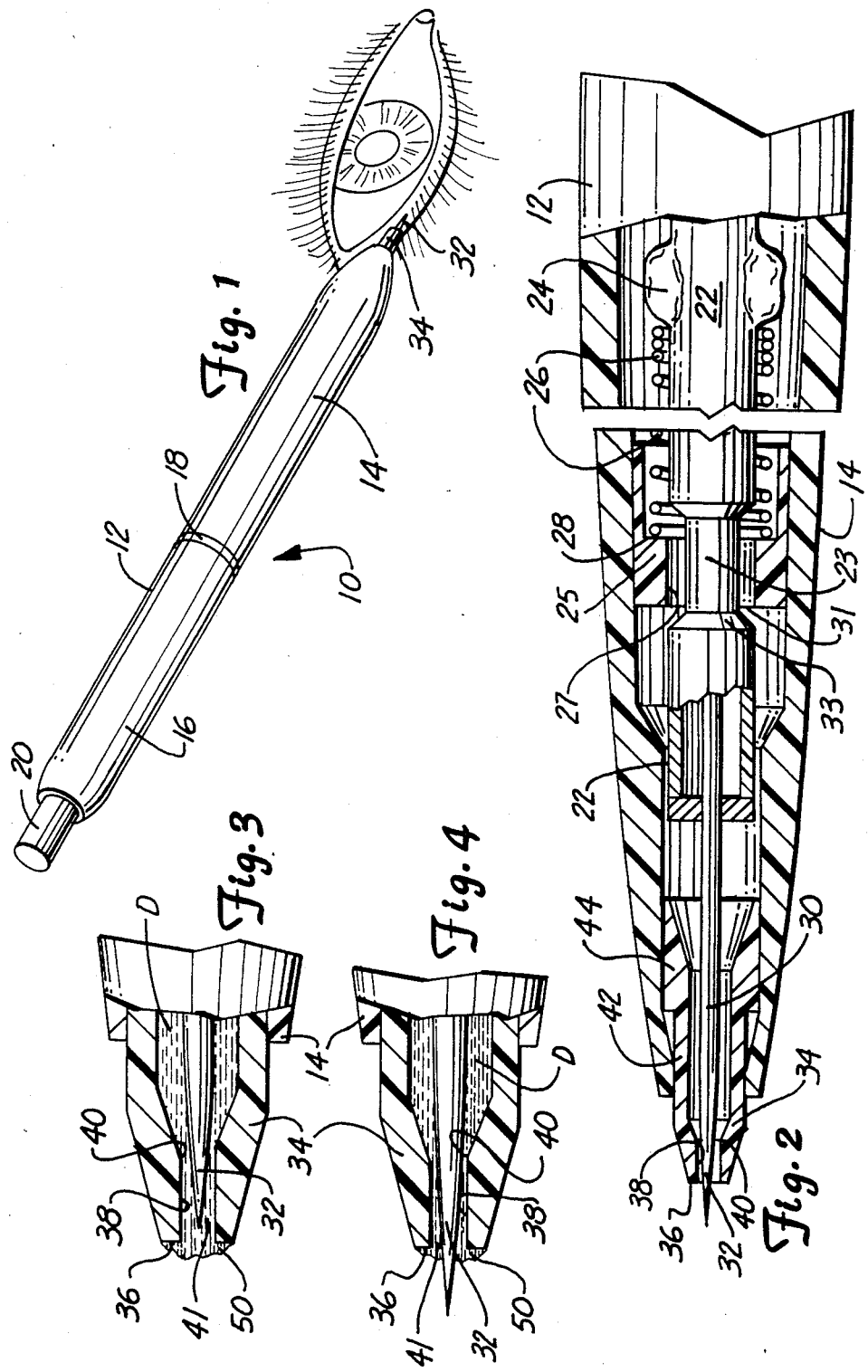

SKIN MARKING DEVICE

FIELD OF THE INVENTION

This invention relates to skin-penetrating devices such as tatoo devices employed to indelibly mark the skin.

BACKGROUND OF THE INVENTION

For centuries, humans, particularly women, have applied cosmetic preparations to the eyelids to emphasize or de-emphasize certain perceived features. In particular, it has been common to apply a dark color to the edges of the eyelids at approximately the point of eyelash growth as an "eye liner". Eye liner materials are commonly applied to the eyes on a daily basis. The application of such materials - commonly by means of a soft pencil or fine brush - requires great care both from the standpoint of obtaining an asthetically pleasing appearance and from the standpoint of avoiding damage to the eye itself from the colored material or from the instruments used to apply the colored material to the eyelid. Hence, applying eyeliner is a job that cannot be asthetically or safely hurried.

Applying permanent coloration to the eyelids has been proposed as a way of avoiding the time-consuming daily chore of applying eyeliner to the eyes. Tatoo needles of the type commonly used for other purposes have been employed to darken the edges of the eyelids, but have not given the precision desired for treatment of the delicate eyelash areas.

SUMMARY OF THE INVENTION

The instant invention provides a hand-held, pencil-like device having an elongated barrel terminating in an open end, and needle means housed within the barrel and having a sharpened end positioned adjacent the open end of the barrel. In one embodiment, means are provided for manually moving the needle means axially within the barrel between an extended position in which the pointed end protrudes a predetermined distance from the open end of the barrel, and a retracted position in which the sharpened end of the needle means is housed within the barrel.

In a preferred embodiment, the barrel includes a desirably separate annular end piece forming the forward open end of the barrel, the end piece being generally tubular and having an outer surface adapted to be held within the tip of the barrel. The needle means includes a needle having a forward end that gradually tapers to a sharp point. The tapered portion of the needle and the cylindrical interior of the barrel tip desirably are so sized that only the tapered section of the needle lies within the cylindrical opening of the barrel tip as the needle means moves between its extended and retracted positions. In this manner, an annular opening is provided and maintained between the barrel tip and the needle, the size of which opening is dependent upon the axial position of the needle means.

A reservoir of a liquid, medically safe dye is positioned within the barrel adjacent the forward open end of the barrel, the dye desirably having a viscosity substantially greater than that of water. The viscosity and other flow characteristics of the dye are matched to the length and diameter of the cylindrical portion of the barrel tip and the needle so the dye can pass by capillary action through the annular opening between the needle and the barrel tip to form a small droplet or bead at the exterior surface of the barrel tip. Once an appropriate exterior dye bead has been formed, the flow of dye substantially ceases until the bead or droplet is removed, as by being touched to and hence transferred to tissue. In this manner one may produce a series of "dots" of dye along the eyelash line of a recipient. With the needle in its extended position, dye is permitted to flow through the annular opening between needle and barrel tip to form the bead at the exterior surface to replenish dye used in the procedure.

Desirably, the needle means is spring mounted within the barrel, and the device includes a finger operated mechanism that may be identical to that used in many ballpoint pens to propel the needle means forwardly to its projecting position and to enable it under spring pressure to be withdrawn into its retracted position within the barrel.

As will now be understood, as the sharpened end of the needle is retracted into the barrel, it comes into contact with and is wetted with the dye; as the needle is again moved into its extended position, it carries dye with it. In this manner, moving the needle axially back and forth between its two positions performs the same function that would be performed were the end of the needle to be dipped in a dye.

In a preferred embodiment, seal means responsive to axial needle movement are provided between the barrel and needle to form an air-tight seal therebetween rearwardly of the dye reservoir when the needle is in its retracted position only. The seal prevents air from entering the barrel rearwardly of the ink reservoir and thus restrains ink leakage forwardly about the needle tip.

The device, with an appropriate supply of dye, provides a completely self-contained eyeliner apparatus. It may be suitably sterilized and packaged, and may be provided with dyes of various shades and hues.

BRIEF DESCRIPTION OF THE DRAWING

FIG. 1 is a perspective view of a device of the invention, showing the device in position to appropriately mark the lid of an eye;

FIG. 2 is an enlarged, broken away cross-sectional view of a device of the invention, with the dye removed;

FIG. 3 is a view similar to that in FIG. 2 but showing the presence of dye when the needle means is in its retracted position; and FIG. 4 is a view similar to that in FIG. 3 but showing the presence of dye when the needle means is in its extended position.

DESCRIPTION OF THE PREFERRED EMBODIMENT

A device of the invention is designated (10) in FIG. 1, and is similar to the design of common ballpoint pens in that it includes a barrel (12) having a finger grip portion (14) and a rearward, "clip" portion (16), the latter often bearing a pocket clip. The barrel portions (14) and (16) are commonly removably threaded together and often are provided with a decorative central spacing band (18). The rearward end portion (16) includes the usual finger push button (20) which, in the case of a ballpoint pen, is pushed once to advance the ballpoint into an extended position and, when pushed again, retracts the ballpoint within the finger gripping portion of the barrel. Such mechanisms are well known and need not be described further. The finger grip portion (14) of the barrel terminates in an opening through which the point of a needle may protrude, as will be described in greater detail below. As used herein, "rearward" refers to that end of the device (10) terminating in the finger push button (20); "forward" refers to the opposite direction.

Referring now to FIG. 2, the finger grip portion (14) of the barrel (12) is hollow and carries within it needle means including a forwardly extending needle (30) carried by an elongated cylinder (22) which is movable axially within the barrel in the same manner as the ink cartridge of a ballpoint pen moves axially within its barrel. The cylinder (22) may be provided with an intermediate portion (23) of reduced diameter, and the rearward end (not shown) of the cylinder (22) operatively engages the push button (20) in a manner identical to that employed with common ballpoint pens.

A hollow, generally cylindrical plug (25) is affixed (as by an adhesive) to the interior of the barrel (14). The plug has an axially extending, forwardly open bore (27) defining a valve seat sized and positioned to receive, as a valve, the elongated cylinder (22) in an air-tight manner when the needle is in its retracted position as shown in FIG. 3. The air-tight seal prevents air from entering rearwardly of the ink supply in the forward end of the barrel, and thus restrains ink leakage forwardly through the open barrel end. The devices of the invention, carrying ink, may thus be shipped or stored in the retracted position to avoid ink leakage. When the needle (30) is in its extended position (FIG. 2), the reduced diameter intermediate portion (23) of the cylinder (22) confronts the bore (27), providing an annular passageway (31) therebetween for air to enter and to permit ink to flow forwardly from the barrel. The diameter of the cylinder (22), if desired, may be larger than the diameter of the bore (27), and the tapered shoulder (33) joining the surfaces of the cylinder (22) and its reduced diameter portion (23) may act as a tapered plug to seal to the forward rim of the bore (27).

At a point along its length, the cylinder (22) is provided with outwardly extending projections (24) and a helical spring (26) is compressed between the projections (24) and an internal, rearwardly facing shoulder (28) formed by an abrupt enlargement of the bore (27). The spring (26), in known fashion, exerts a rearward force upon the cylinder (22), and the latter can be moved forwardly or rearwardly within the barrel simply by repeated pressing of the button (20). As noted above, this mechanism is so well known as to require no further description.

Extending from the forward end of the cylinder (22) is a needle (30) having a gently tapered, sharpened forward end (32). The shank of the needle (30) may be welded or otherwise affixed to the cylinder (22).

The barrel, in a preferred embodiment, includes a hollow, generally cylindrical tip (34) formed as a separate piece and inserted in the finger grip portion (14) of the barrel, the tip (34) including a portion which extends forwardly and terminates in a forwardly facing generally flat or gently rounded annular surface (36). As will be explained below, the surface (36) serves several functions. The tip (34) includes a narrow bore (38) having a diameter sufficient to enable the tapered forward end portion (32) of the needle to assume its extended (FIG. 4) position without permitting the needle shank to completely block or plug the bore (38). As shown best in FIGS. 3 and 4, the bore (38) terminates rearwardly in a shoulder designated (40), the needle (30) and the shoulder (40) defining between them an opening (41), generally annular when the needle is centered, through which dye from within the barrel may flow forwardly. In the embodiment depicted in FIG. 2, the tip (34) extends rearwardly within the finger grip portion (14) of the barrel, and includes an intermediate cylindrical portion (42) and a rearward portion (44) of enlarged diameter. The cylindrical portion (42) of the tip (34) fits snugly within the open end of the barrel portion (14), and the enlarged portion (44) of the tip bears forwardly against the inwardly tapering walls of the barrel to precisely locate the tip (34). The length of the needle means (including the needle (30) and cylinder (22)), and the position of the tip (34), can be varied as needed so that the forward end (32) of the needle, in its extended position, extends perhaps a millimeter from the end (36) of the barrel tip (34) and in its retracted position is sheltered completely within the tip (34).

A dye "D" suitable for injection beneath the surface of the skin of a patient is placed within the device at its forward end, the dye encircling the forward end portion (32) of the needle within the tip (34). A large reservoir of dye is not needed; only a small amount of dye is sufficient to provide the desired eyeliner effect to both eyes of a patient. Commonly, the device of the invention will be discarded after use rather than taken apart, cleaned, refilled and resterilized.

The dye to be employed may be any of the dyes that have been previously used for tattooing. One dye that has given excellent results can be made from very finely ground synthetic magnetite ($FeO \cdot Fe_2O_3$) dispersed in a suitable liquid vehicle such as USP glycerin or a glycol base such as polyethylene glycol (PEG-400). A suitable dye may contain about fifty percent by weight of the magnetite. Other ingredients may be added as required. The magnetite, available as a very fine powder, can be simply mixed into the polyethylene glycol or glycerin base through use of a high speed mixer. Various other dyes and inks can be used as well, of course. The pigment portion of the dye may be present as a dispersion of a solid (e.g. magnetite) or liquid in the liquid vehicle, or may be wholly or partially dissolved in the liquid vehicle. The dye must, of course, be sterile and physiologically acceptable. The dye has suitable flow properties to enable it to be drawn forwardly through the generally annular opening (41) by capillary action.

The small, generally annular opening between the tip (34) of the barrel and the outer surface of the needle can be varied by movement of the needle axially within the tip. The walls of the needle at its forward end diverge rearwardly, and as the needle is moved axially forwardly in the barrel, it occupies an increasing proportion of the cross-sectional area of the bore (38). The opening between the tapering needle wall and the bore is such as to promote flow of the dye (labeled "D") forwardly through capillary action. When the needle is in its retracted position as shown in FIG. 3, and assuming the needle is periodically moved to its extended position to permit air flow through the annular opening (31), the dye, having suitable viscosity and flow properties, will collect as a "bead" or droplet (50) at the forward end of the tip (34). As the forward end (36) of the barrel tip is repeatedly touched against the surface of the skin of a patient, the bead (50) is repeatedly drawn from the tip by the skin, whereupon the bead is replenished through forward flow of the dye (D). Similarly, when the needle (30) is in its extended position as shown in FIG. 4, a bead (50) continues to form on the forward, annular end (36) of the barrel tip and is drawn off by repeated contact with the skin as the needle repeatedly penetrates the skin.

When forced into the skin of a patient, the needle tip (32) carries with it a small quantity of the dye which remains in the microscopic wound thus formed and thereafter appears as an extremely small, individually barely perceptible "dot". The provision of many such "dots" in close proximity to one another and generally on and slightly to either side of an imaginary line provides a visually pleasing perceived line on the skin.

As previously mentioned, the devices of the invention preferably are supplied in sterile, packaged form as completely self-contained instruments. The patient is readied by a thorough washing of the eyelids and adjacent skin portions, followed by the appropriate administration of an anesthetic such as xylocaine or novocain. From an aesthetic standpoint, the small "dots" should be provided in the eyelids closely adjacent to the line from which the eyelashes protrude and for this reason, the use of a surgical microscope is recommended. The dots are sufficiently close together as to cause one to perceive them as a line.

The device of the invention is removed from its sterile wrapper and the finger button (20) may be pushed several times to extend and retract the needle and to promote the flow of dye to the barrel tip. Once the dye flow has begun, the needle may remain in its extended position, and the needle is repeatedly forced gently into the skin of the eyelid, carrying with it the dye. As mentioned previously, only a small length of needle - on the order of one millimeter - is permitted to extend beyond the tip of the barrel, and the forwardly facing annular surface of the barrel tip thus also acts as a safety stop which encounters the surface of the skin and prevents the needle from being thrust into the skin to a distance greater than the distance the needle itself protrudes from the forward end of the barrel. Dye which flows forwardly through the generally annular opening between the needle and the barrel tip forms a small bead or droplet at the forward end of the barrel tip, as previously described, and each time the barrel tip encounters the skin, the bead is drawn off to the skin to be replenished from the reservoir within the barrel. The penetration of the needle into the skin carries with it dye from the surface of the skin; commonly a small "puddle" of dye is thus formed upon the skin through which the needle is repeatedly thrust. The eyelid is wiped often with gauze to remove accumulated dye.

When the procedure has been completed, an antiseptic cream may be applied to the eyelids as desired to promote healing and to reduce swelling; experience indicates that careful attention to cleanliness of the skin surface of the eyelid and careful use of the device of the invention commonly results in very little swelling or discomfort to the patient.

Although the device has been described primarily with reference to placing a permanent visible line upon the lids of the patient for cosmetic purposes, the device is clearly capable of intradermal placement of a dye elsewhere on the body, such as on the eyebrows.

Thus, the invention provides a self-contained device which can be sterilized and maintained in sterile packaging prior to use, and which can be provided in a variety of colors, shades and hues and desired. A tip end of the barrel acts both as an applicator for applying dye to the skin and also as a safety stop to limit the degree to which the needle tip may enter the skin. The size of the annular opening between the tapering needle end and the barrel tip is a function of the axial position of the needle end within the tip and thus be varied as desired.

While a preferred embodiment of the present invention has been described, it should be understood that various changes, adaptations and modifications may be made therein without departing from the spirit of the invention and the scope of the appended claims.

What is claimed is:

1. A device for the intradermal placement of a dye, comprising a tubular barrel adapted to be held by the fingers; needle means carried by the barrel and including a needle having a pointed forward end, the barrel terminating forwardly in a hollow tip through which the pointed end of the needle forwardly protrudes, the barrel tip having an annular forwardly facing surface positioned to contact the skin of a patient and limit the distance to which the needle can be thrust forwardly into the skin, the needle and barrel opening defining a generally annular opening therebetween, and a dye carried within the barrel in flow communication with the generally annular opening, the dye having viscosity and flow properties enabling it to flow forwardly through the annular opening and to collect as a forwardly-exposed bead upon the forwardly facing annular surface of the barrel, whereby dye from the bead is deposited on the skin of a patient when the annular surface is touched to the skin to form a puddle of dye upon the skin through which the needle may be thrust into the skin to deposit dye therewithin.

2. The device of claim 1 including means permitting said needle to move axially between an extended position in which the tip of the needle protrudes from the tip of the barrel and a retracted position in which the tip of the needle is sheltered within the barrel tip.

3. The device of claim 2 wherein the sharpened end of said needle tapers gradually to a point and wherein the barrel tip has a central bore sized to receive the needle and to provide said annular opening therebetween, the size of the annular opening being a function of the axial position of the needle.

4. The device of claim 2 where the barrel is sized to be held by the fingers in substantially the same fashion that a pencil is held while writing, the device including finger operable means for moving the needle means between the extended and retracted positions.

5. The device of claim 2 including seal means responsive to axial movement of the needle means to provide an air tight seal within the barrel rearwardly of the dye when the needle means is in its retracted position, thereby restraining forward flow of dye through the barrel tip.

6. A self-contained, sterile, readily packaged device for the intradermal placement of a dye, comprising a tubular barrel adapted to be held in the fingers and having a tip providing a narrow opening at one end, needle means comprising a needle having a pointed end and carried by the barrel, the needle means being moveable axially within the barrel between an extended position wherein the pointed end of the needle protrudes from the narrow barrel opening and a retracted position wherein the pointed end is positioned within the barrel tip, the needle in its extended position and the barrel tip defining a generally annular opening therebetween, and liquid dye carried within the barrel and positioned therewithin to feed through the generally annular opening between the needle and barrel tip, the barrel including a generally annular skin-contacting surface about the narrow opening and adapted to contact the skin of a patient and to limit the distance within which said pointed end of the needle can protrude into the skin, said annular surface being positioned to receive dye from said generally annular opening and to form a bead thereon, dye from said bead being deposited upon the skin of a patient when the annular surface is touched to the patient's skin.

7. The device of claim 6 wherein the barrel is sized to be held by the fingers of one hand in the same fashion that a pencil is held, the device including manually operable means for moving the needle means between the extended and retracted positions.

8. The device of claim 6 including seal means responsive to axial movement of the needle means to provide an airtight seal within the barrel rearwardly of the dye when the needle means is in its retracted position, thereby restraining forward flow of dye through the barrel tip.

9. The device of claim 8 in which said seal means comprises means carried internally of the barrel and defining a valve seat, and means carried by the needle means and defining a valve receivable in the valve seat when the needle means is moved into its retracted position.

* * * * *